United States Patent [19]
Sugiyama

[11] Patent Number: 5,108,170
[45] Date of Patent: Apr. 28, 1992

[54] PERIMETRIC INSTRUMENT
[75] Inventor: Akihiro Sugiyama, Tokyo, Japan
[73] Assignee: Kabushiki Kaisha Topcon, Japan
[21] Appl. No.: 635,303
[22] Filed: Dec. 28, 1990
[30] Foreign Application Priority Data
  Dec. 29, 1989 [JP] Japan .................. 1-340246
  Dec. 29, 1989 [JP] Japan .................. 1-340247
[51] Int. Cl.⁵ .............................. A61B 3/02
[52] U.S. Cl. ............................ 351/226; 351/224
[58] Field of Search .............. 351/224, 225, 226
[56] References Cited
  U.S. PATENT DOCUMENTS
  4,561,738 12/1985 Humphrey et al. .......... 351/226

Primary Examiner—Rodney B. Bovernick
Attorney, Agent, or Firm—Brumbaugh, Graves, Donohue & Raymond

[57] ABSTRACT

The present invention relates to a perimetric instrument for measuring a range of a visual field of an eye of a man, and more particularly to a perimetric instrument which includes an abnormal visual field pattern analogical inferring section using a multilayer neural network and can analogically infer an abnormal visual field pattern of a measurement object person. Further, the present invention provides a perimetric instrument which can automatically make a determination of an additional target. In particular, according to the present invention, a multilayer neural network including an input layer, hidden layers and an output layer introduces a neural weight ratio which is determined based on responses when the visual field is normal and abnormal, and as a response from a responding section is inputted to the input layer while an output from the output layer is sent out to an analogical inferring section, the analogical inferring section can analogically infer an abnormal visual field pattern of the measurement object person. Accordingly, it is possible to help judgment of an abnormal visual field pattern by a measurer, and since also labor, time and so forth of the measurer are reduced, burdens to the measurer and them easurement object person can be reduced remarkably.

5 Claims, 17 Drawing Sheets

LEVEL 0 :
LEVEL 1 ❖
LEVEL 2 H
LEVEL 3 +
LEVEL 4 ▫

- BASIC MEASUREMENT POINT
- o ADDITIONAL MEASUREMENT POINT

| | RESPONSE |
|---|---|
| ADDITION 1 | 3 |
| ADDITION 2 | 2 |
| ADDITION 3 | 5 |

| | RESPONSE | INPUT DATA |
|---|---|---|
| NO. 9 | 2.5 | $\frac{1}{3}(2.5 + \frac{r_1}{r_1} \times 3 + \frac{r_1}{r_2} \times 2)$ |
| NO. 10 | 2 | $\frac{1}{2}(2 + \frac{r_4}{r_4} \times 2)$ |
| NO. 11 | 3 | $\frac{1}{3}(3 + \frac{r_3}{r_3} \times 3 + \frac{r_3}{r_5} \times 5)$ |
| NO. 12 | 4 | 4 |

WHEREIN $r_1 \leq r_2$
$r_3 \leq r_5$

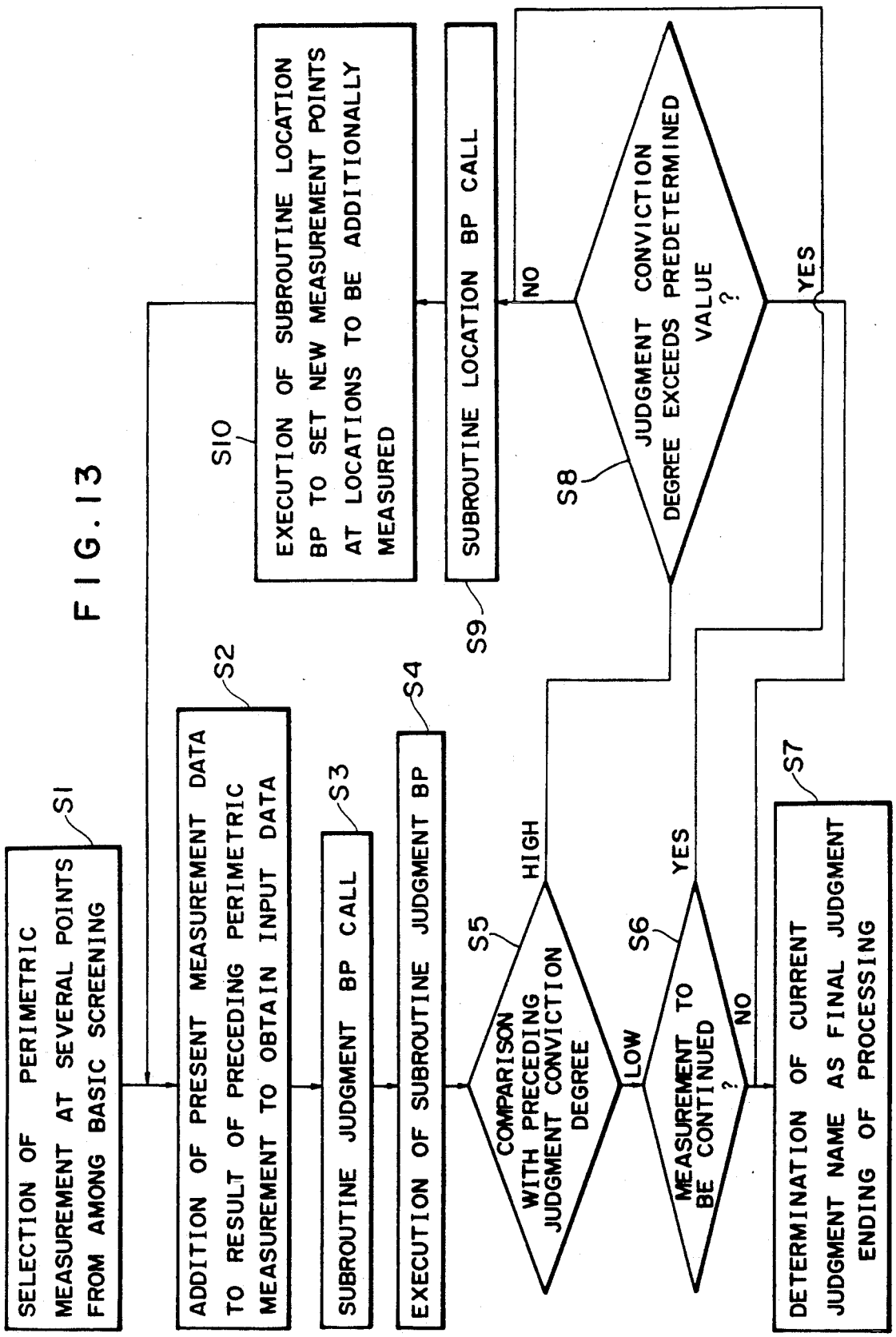

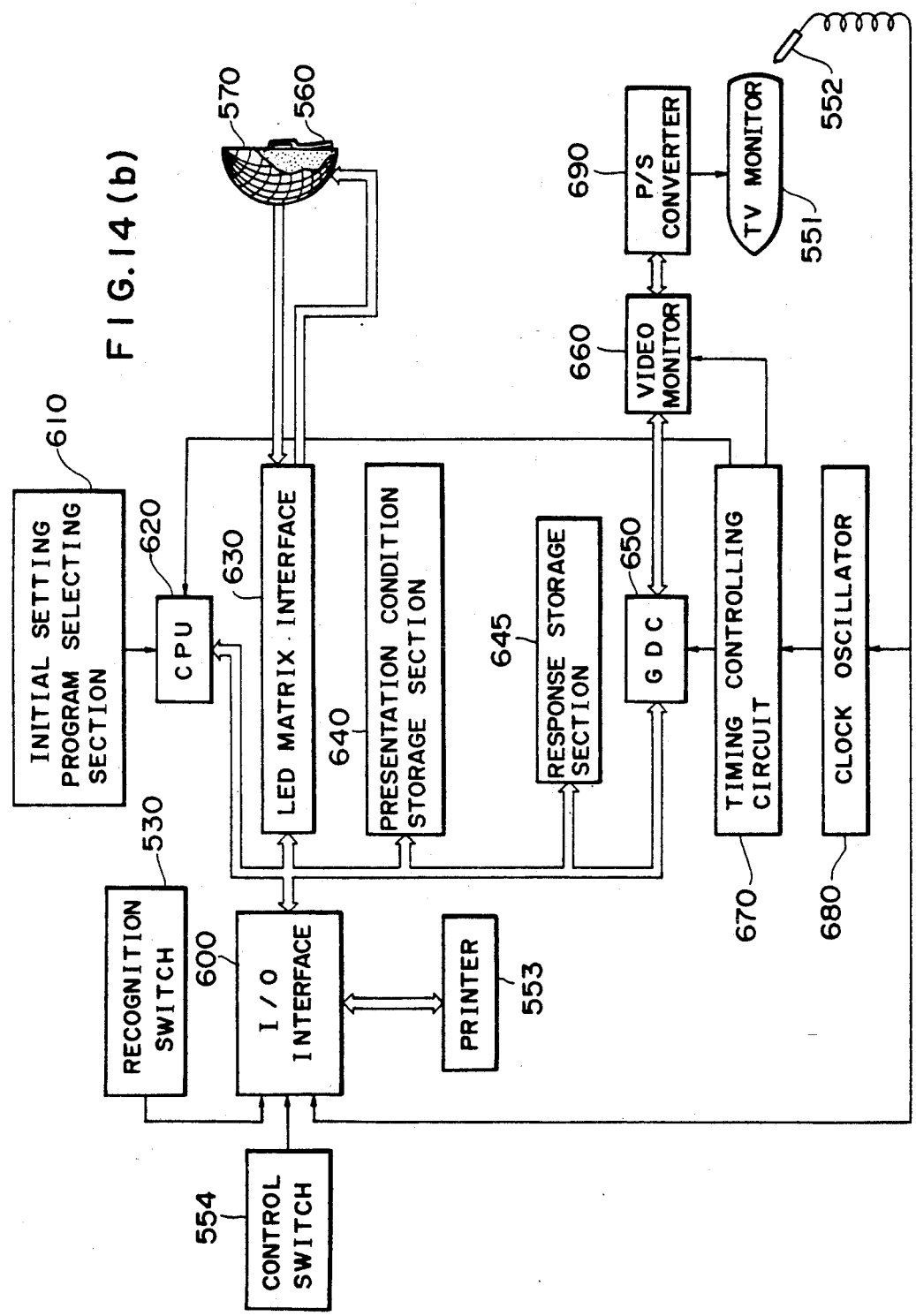

PERIMETRIC INSTRUMENT

BACKGROUND OF THE INVENTION

This invention relates to a perimetric instrument for measuring a range of a visual field of a man, and more particularly to a perimetric instrument which includes an abnormal visual field pattern analogical inferring section employing a multilayer neural network and can analogically infer an abnormal pattern of a visual field of a measurement object person and besides can automatically determine an additional target.

Measurement of a visual field is considered very important among clinical inspections of the ophthalmology and is utilized for the diagnosis of glaucoma, detached retinas, a brain injury, hysteria and so forth.

A visual field is "a range over which an eye is capable of seeing when it gazes steadily at a point", but since the sensitivity of the retina is not uniform in the range of a visual field, a visual field is accurately defined as "a sensitivity distribution of the visual sense". Perimetric instruments used for such clinical inspections include a dynamic quantitative perimetric instrument and a static quantitative perimetric instrument.

A line which interconnects different points of the retina at which the sensitivity is equal is called an equal sensitivity line isopter, and if various targets having different brightness values and sizes are moved from a periphery to the center and figures formed by interconnecting such points at which the targets are first recognized (or missed) are obtained, then various isopters can be obtained. According to a dynamic quantitative visual field, a visual field table is obtained by suitably selecting an isopter, and for example, a perimeter wherein a target is presented with various brightness values on a semicircular screen and a brightness (threshold value) at which a measurement object person begins to feel the target is found out at the individual positions and then such brightness values are indicated in a figure is a Goldmann perimeter. A measurer makes use of the figure to judge abnormality of a visual field (location at which the sensitivity is low) of the measurement object person.

A method of measuring a sensitivity of the retina with a reciprocal number to a brightness when a target is recognized at first while the brightness is raised with the position of a visual field held fixed is static quantitative visual field measurement.

Those perimetric instruments have two types including a manual type and an automatic type.

Manual measurement is a method wherein a measurer presents a target and determines a next measurement point while confirming a response to the target.

On the other hand, automatic measurement is a method wherein an order of presentation of targets is determined in advance in accordance with a program or the like and presentation is proceeded in accordance with the order. With such automatic perimeter, also static quantitative measurement by a stimulus above a threshold value can be performed readily. Static quantitative measurement by a stimulus above a threshold value is a method wherein stimulating light brighter than a threshold value is presented and it is confirmed that the stimulating light can be seen.

In order to precisely judge abnormality of a visual field, it is desirable to measure efficiently at inspection positions in accordance with symptoms. In this regard, a perimeter of the manual type has an advantage that it can measure at measuring positions in accordance with symptoms, but it has a drawback that considerable experience and attentiveness are required for a measurer such that various abnormal visual field patterns are grasped sufficiently and accordingly burdens to the measurer are very heavy. If it is assumed that the range of 360 degrees of a visual field is inspected for each 30 degrees using a Goldmann perimeter, then a target must be moved repetitively to 12 directions, and besides, in case an abnormal portion is found out, the neighborhood of the portion must be measured further particularly. Consequently, there is another drawback that very much time is required. Accordingly, there is a serious problem that not only a measurer is compelled by much labor but also a feeling of fatigue is given to a measurement object person.

With an automatic perimeter of the automatic type, burdens to a measurer are reduced because the apparatus itself presents a target automatically, but there is a problem that it cannot measure a measuring points in accordance with symptoms.

Thus, appearance of a perimetric instrument is demanded strongly which can reduce burdens to a measurer and a measurement object person by analogically inferring an abnormal visual field pattern of the measurement object person and helping the diagnosis of the measurer and further measurement points can be determined in accordance with an abnormal visual pattern obtained by such measurement.

BRIEF DESCRIPTION OF THE DRAWINGS

The drawings show a perimetric instrument of an embodiment of the present invention.

FIG. 13 is a view illustrating operation of a third embodiment;

DETAILED DESCRIPTION OF THE INVENTION

Figure 1:
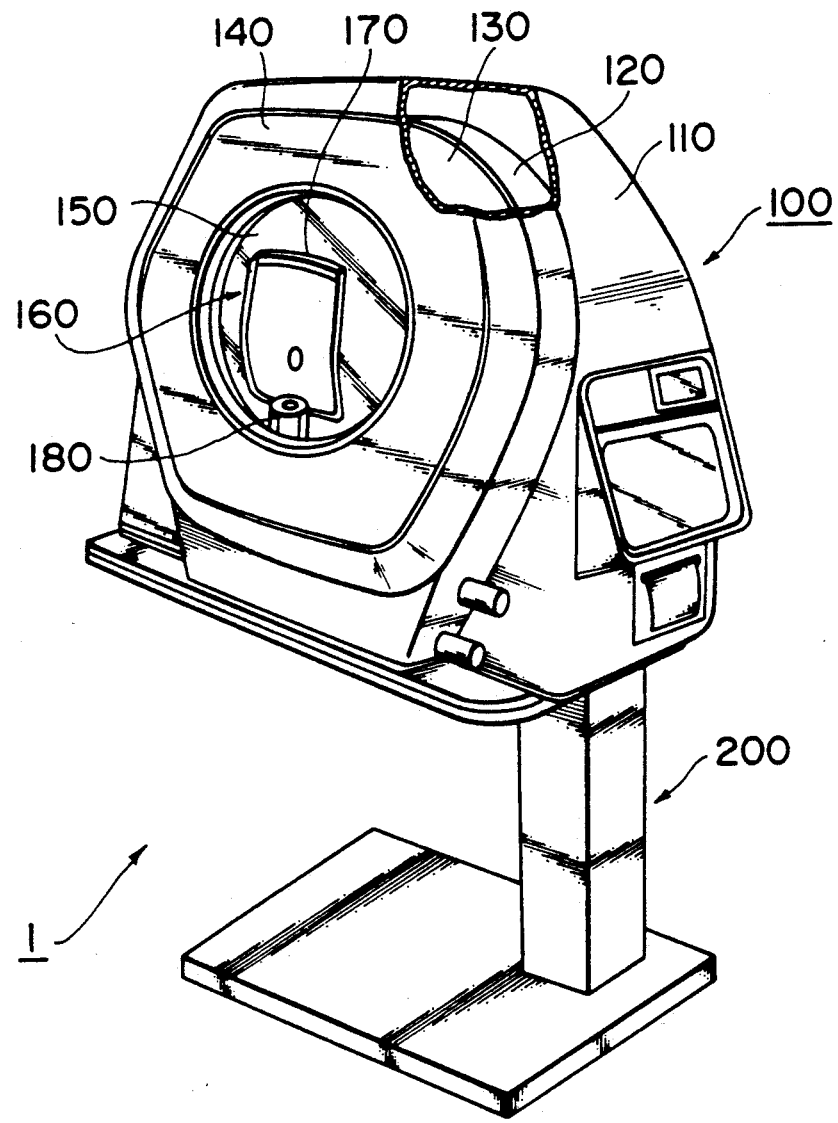
FIG. 1 is a view showing construction of an appearance of the present embodiment.
Figure 2A:
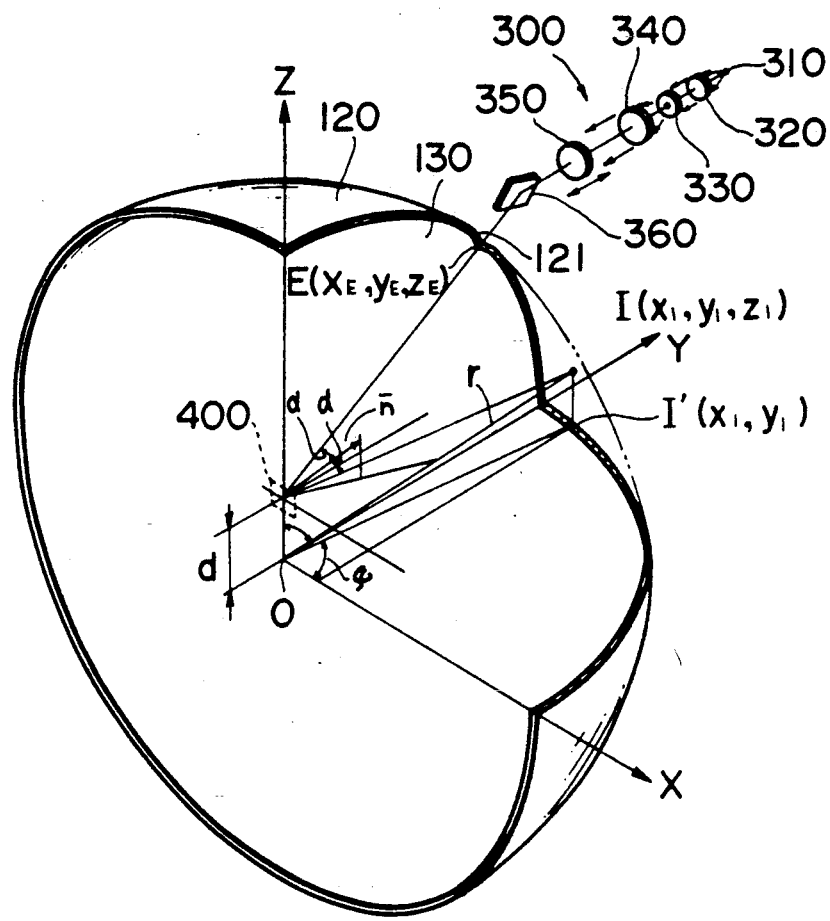
FIGS. 2 (a-c) are views illustrating construction of essential part of the present embodiment.
Figure 2B:
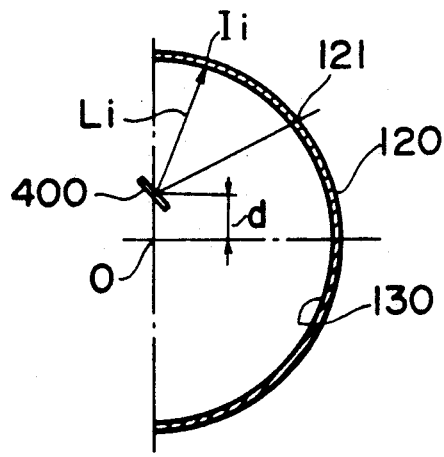
Figure 2C:
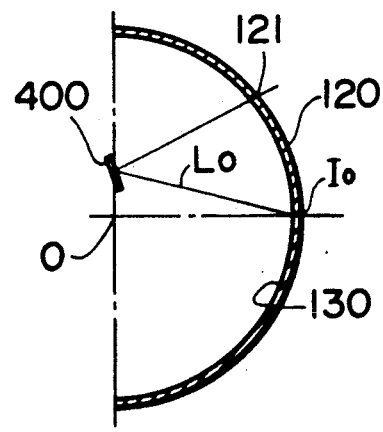

Embodiments of the present invention will be described with reference to the drawings. FIGS. 1 and 2 are views illustrating a mechanical construction of a perimetric instrument 1, and the perimetric instrument 1 is constituted from a perimetric instrument body 100 and a base 200. The perimetric instrument body 100 includes a housing 110, and a substantially hemispherical dome 120 is provided on the housing 110 and an inner face of the dome 120 serves as a projection screen 130. A panel 140 is provided at a front portion of the dome 120 and has a face receiving hole 150 formed therein, and a face receiving member 160 for the fixation of the face is provided in the face receiving hole 150. Then, a forehead receiver 170 and a chin receiver 180 are mounted on the face receiving member 160. Meanwhile, an eye to be measured is positioned at a location in the proximity of the spherical center 0 of the projection screen 130 including the spherical center O.

A projecting optical system 300 is provided on the rear face side of the dome 120 as shown in FIG. 2 in the housing 110. The projecting optical system 300 is constituted from a target projecting light source 310, a condensing lens 320, a target 330, a collimator lens 340, a projecting lens 350, and a reflecting mirror 360, 360. Here, the target projecting light source 310, condensing lens 320, target 330 and collimator lens 340 constitute a first optical system for emitting target light as a parallel beam of light. The projecting lens 350 and reflecting mirror 360 constitute, together with a rotary mirror 400 which will be hereinafter described, a second optical system for receiving a parallel beam of light and introducing target projection light to a target presentation location I of the projection screen 130 by way of a location in the proximity of the spherical center 0 except the spherical center O. A guide hole 121 is perforated in the dome 120. Target projection light reflected by the reflecting mirror 360 passes through the guide hole 121 and is introduced to the rotary mirror 400.

The rotary mirror 400 is provided at a location in the proximity of the spherical center O except the spherical center O, and if the rotary mirror 400 is rotated, then the target presentation location I is changed.

Figure 3:
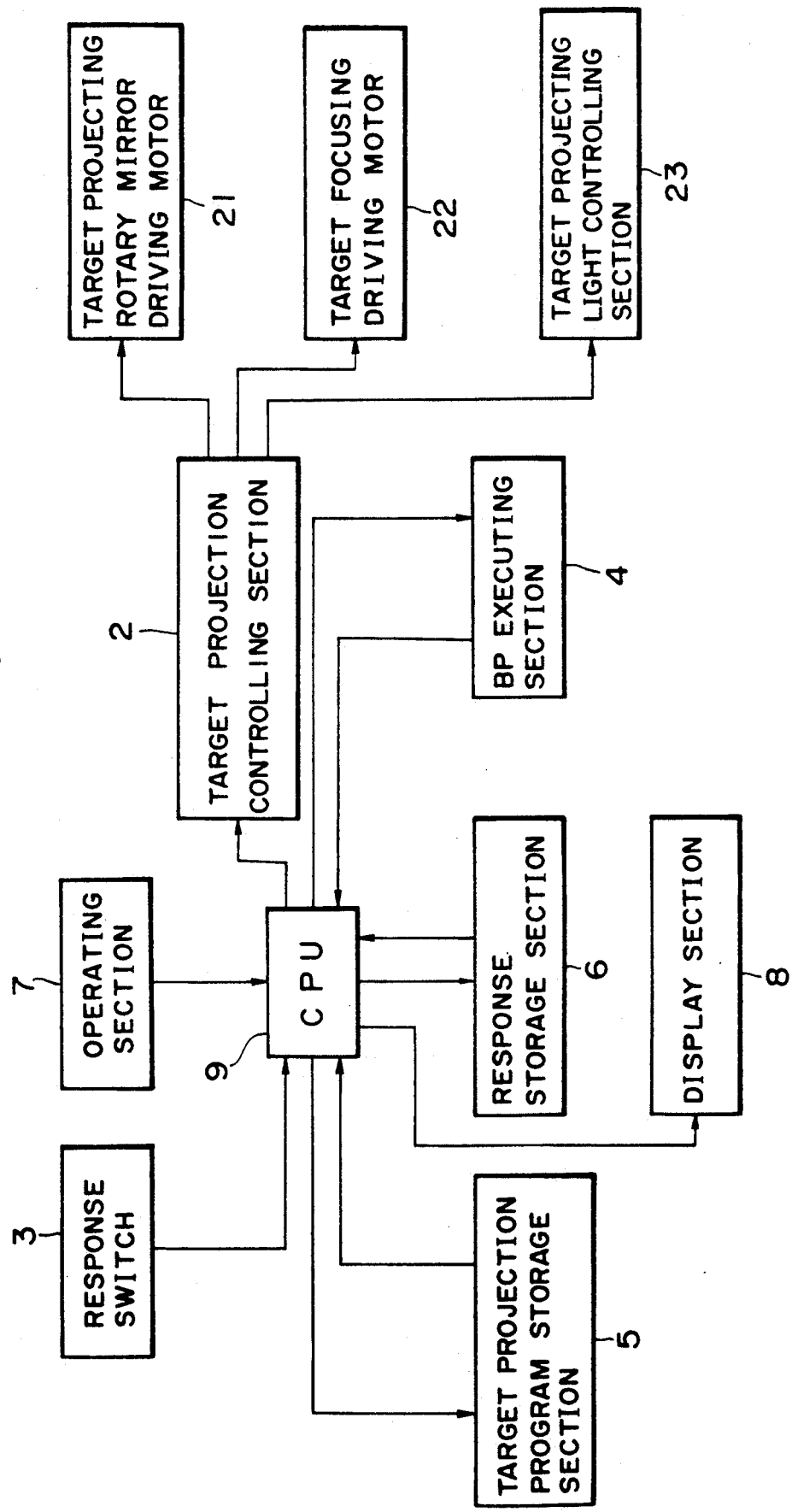
FIG. 3 is a view illustrating an electric construction of the present embodiment.

Subsequently, an electric construction of the perimetric instrument 1 of the present embodiment will be described with reference to FIG. 3. The electric construction of the perimetric instrument 1 is constituted from a visual field projection controlling section 2, a response switch 3, a BP (back propagation) executing section 4, a target projection program storage section 5, a response storage section 6, an operating section 7, a display section 8 and a CPU 9. The visual field projection controlling section 2 is provided to control a target projecting mirror driving motor 21, a visual field focusing driving motor 22 and a target projecting light controlling section 23 and corresponds to a target presenting section. The target projecting rotary mirror driving motor 21 is provided to drive the rotary mirror 400 and can change the target presentation location I by rotating the rotary mirror 400. The target focusing driving motor 22 is provided to move the image pickup lens 350 and can change the distance L from the center of rotation of the rotary mirror 400 to the target presentation location I. In particular, if the target photographing rotary mirror driving motor 21 is driven to rotate the rotary mirror 400, the distance L from the center of rotation of the rotary mirror 400 to the target presentation location I is changed. In order to correct the change of the distance L, it is necessary to drive the target focusing driving motor 22 to move the image pickup lens 350 in a direction of its optical axis. As a result, an image of the target which is changed little in size and brightness irrespective of a change of the target presentation location I can be displayed on the projection screen 130. The target projecting light controlling section 23 is provided to control lighting of the target projecting light source 310 and not only can perform switching between lighting and extinction but also can change the brightness (intensity) of the light source by adjusting the voltage to the light source. Then, the brightness of the target on the projection screen 130 can be changed by adjusting the intensity of the target projecting light source 310.

The response switch 3 corresponds to a responding section and is provided to input whether or not a measurement object person has recognized the target. The response switch 3 is preferably of the type wherein it is operated by a measurement object person itself, but such construction may be employed wherein, in case the measurement object person is a child or an old person, a measurer receives recognition from the measurement object person and operates the response switch 3.

The BP executing section 4 is provided to execute judgment based on back propagation using a neural weight ratio determined in advance in accordance with a normal response and typical responses when the visual field is abnormal. Accordingly, matching between a typical response and so forth when the visual field is abnormal and a response of a measurement object person can be performed by way of a neural network to analogically infer an abnormal visual field pattern of the measurement object person.

A neural weight ratio which is utilized by the BP executing section 4 is determined in advance in accordance with a normal response and typical responses when the visual field is abnormal using a neural network similar to the neural network of the BP executing section 4 which will be hereinafter described.

The target projection program storage section 5 has stored therein programs for determining target presentation conditions for the measurement of a visual field and can control the brightness of the target, the position of an index, the lighting time and so forth to desired values. The target projection programs may adopt, for example, a screening measurement program, a meridional program, a program for glaucoma and so forth.

The response storage section 6 is provided to store therein presence or absence of recognition of the target by a measurement object person. In particular, the response storage section 6 is provided to store therein whether or not the response switch 3 has been started with respect to the target presented. The operating section 7 is provided to effect operation of the entire perimetric instrument 1 and is constituted from various control switches, a light pen and so forth. The display section 8 is constituted from a TV monitor, a printer apparatus and so forth and can display a kind of the target projected on the projection screen 130, an index distribution, and an instruction and so forth inputted by way of the control switches and so forth and further can display a result of analogical inference of an abnormal visual field pattern of a measurement object person.

The CPU 9 executes various calculation controls of the perimetric instrument 1.

In the present embodiment constituted in such a manner as described so far, if a measurement starting instruction is inputted by way of the operating section 7, the CPU 9 reads in a control program from the visual field projection program storage section 5 and executes the control. The CPU 9 controls the target projection controlling section 2 in accordance with the control program to drive the target projecting light controlling section 23. The CPU 9 further controls the target photographing rotary mirror driving motor 21 to rotate the rotary mirror 400 to determine the position of the target. Also the CPU 9 drives the target focusing motor 22 in response to rotation of the rotary mirror 400 to adjust the brightness and the size of the target so that they may not be varied. The response storage section 6 stores a response of a measurement object person therein. Then, the CPU 9 executes matching with the normal visual field pattern and the typical abnormal visual field patterns to analogically infer an abnormal visual field pattern. Then, the thus analogically inferred abnormal visual pattern and so forth are displayed on the display section 8.

Subsequently, a construction of a multilayer neural network constituting the neural network will be described in detail with reference to FIG. 4.

A neural network is constituted from a plurality of nerve cells (neurons), and a neuron is constituted from a cell body, a dendrite (signal inputting portion) and an axon (signal outputting portion). The axon (signal outputting portion) is synapse coupled to the dendrite of another neuron so that a network is formed.

Figure 4:
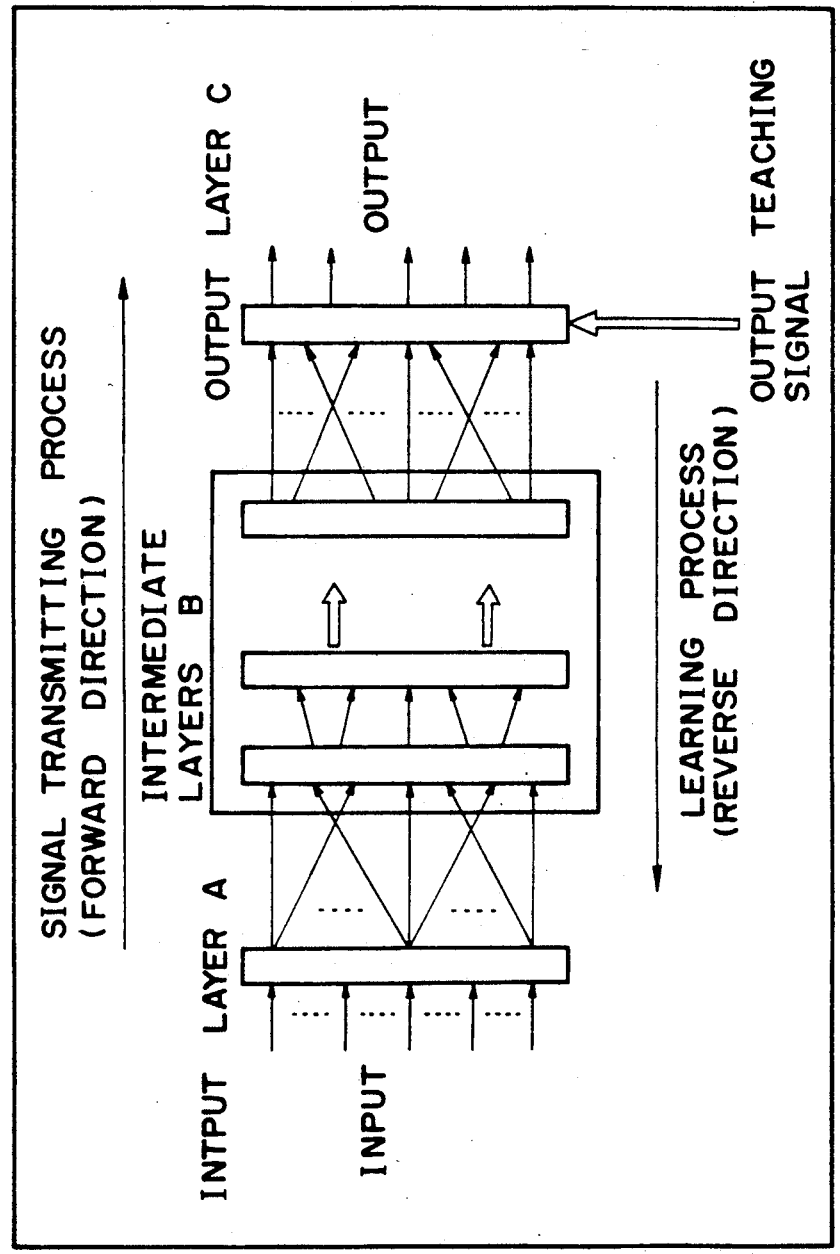
FIG. 4 is a view illustrating a multilayer neural network.

Then, a learning method which is applied to such neural network is a method called back propagation method, and the structure of the neural network is a multilayer structure of an input layer A, intermediate layers B and an output layer C as shown in FIG. 4. It is to be noted that there is no coupling between units in any layer while there are couplings between different layers.

Since a neuron can be regarded as a non-linear element of the multi-input-single output type, it can be regarded, in other words, as an element having a "threshold value action". In particular, if the total amount of inputted signals becomes higher than a threshold value, then the output pulse becomes on, but if it is lower than the threshold value, then the output is off.

Accordingly, an output signal net with respect to input signals $S_1, S_2, S_3, \ldots,$ and $S_n$ is represented in weighted sum of products as $$\text{net} = \Sigma W_i \times S_i \quad (1)$$

In particular, the structure of the network can be changed by changing the weight (W). It is to be noted that the weight (W) assumes a positive or negative value or zero which represents absence of a coupling. Meanwhile, a sigmoid function is applied as an input/output characteristic function. The sigmoid function is a differentiable pseudo linear function, and a function represented, for example, by $$fi = \frac{1}{1 + e^{-neti}} \quad (2)$$

can be adopted. The value range of the function is from 0 to 1, and the value approaches 1 as the input values increase, but the value approaches 0 as the input values decrease. Then, the value is 0.5 when the input values are 0. Subsequently, algorithm of a rule of back propagation learning will be described. It is to be noted that the number of the intermediate layers B may be any number, and a network is assumed which has no feedback coupling (layer-to-layer coupling). Here, an intermediate layer B is sometimes called hidden layer, that is, hidden layer.

(a) First, an input signal such as an image pattern is inputted to the input layer.

(b) Then, condition changes of individual neurons in the process of transmission of the signal from the input layer A toward the output layer C are calculated successively.

(c) Where an output of the j-th neuron of the output layer C obtained in (b) described above is represented by $O_{pj}$ and a desirable output (teaching signal) of the neuron with respect to the input signal is represented by $T_{pj}$, a square error of the following expression is defined as an evaluation function and calculated. It is to be noted that a given image pattern is represented by p.

$$E_p = \tfrac{1}{2}\Sigma(T_{pj} - O_{pj})^2 \quad (3)$$

(d) The synapse couplings, that is, the weight ratio, of the network is changed so that the evaluation function may have a minimum value (preferably the smallest value) (that is, so that the actual output may approach a desirable output as far as possible).

In particular, the strength of all couplings should be changed so that the error in output may be reduced. Here, a changing amount of the weight $W_{ji}$ when the image pattern p is given is defined as $$\Delta_p W_{ji} \alpha - \frac{\partial E_p}{\partial W_{ji}} \quad (4)$$

If the expression is deformed, then $$\Delta_p W_{ji} = \eta \delta_{pj} O_{pi} \quad (5)$$

It is to be noted that $O_{pi}$ is an input value from a unit i to another unit j, and $\delta_{pj}$ is different depending upon whether the unit j is an output unit or an intermediate unit, and in case it is an output unit, $$\delta_{pj} = (t_{pj} - O_{pj}) f'(\text{net}_{pj}) \quad (6)$$

but in case it is an intermediate unit, $$\delta_{pj} = f'(\text{net}_{pj}) \sum_k \delta_{pk} W_{kj} \quad (7)$$

The expression (7) is a recurrent function.

The basic algorithm of the back propagation method is such as described so far, and learning of the individual synapse couplings (modification of the weight ratio) proceeds from the output layer toward the input layer reversely to that upon propagation of a signal. This is the reason while the method is called back propagation. According to the back propagation method, a calculation of $\Delta W$ starts from the output layer and proceeds to units of the intermediate layers. A calculation cannot be performed for an intermediate unit unless $\Delta W$ at a preceding stage is not determined. (Since it is recurrent,) Accordingly, a calculation is impossible without going back to the input layer at the last. Therefore, according to the back propagation method, data for the learning are inputted, and a result is outputted (forwardly). Subsequently, the strength of couplings is changed so that the error of the result may be reduced (reversely). Then, the data for the learning are inputted again. Those steps are repeated to determine $\Delta W$ so that the error may be minimum.

Here, a general expression of $\Delta W$ is given by $$\Delta W_{ji}(n+1) = \eta \delta_{pj} O_{pj} + \alpha \Delta W_{ji}(n) \tag{8}$$

where n is a number of learning times, and the first term of the right-hand side is $\Delta W$, while the second term is an additional term for preventing vibrations of an error to accelerate convergency.

Subsequently, the back propagation method adopted for the learning of the multilayer neural network will be described with reference to FIG. 5.

Figure 5:
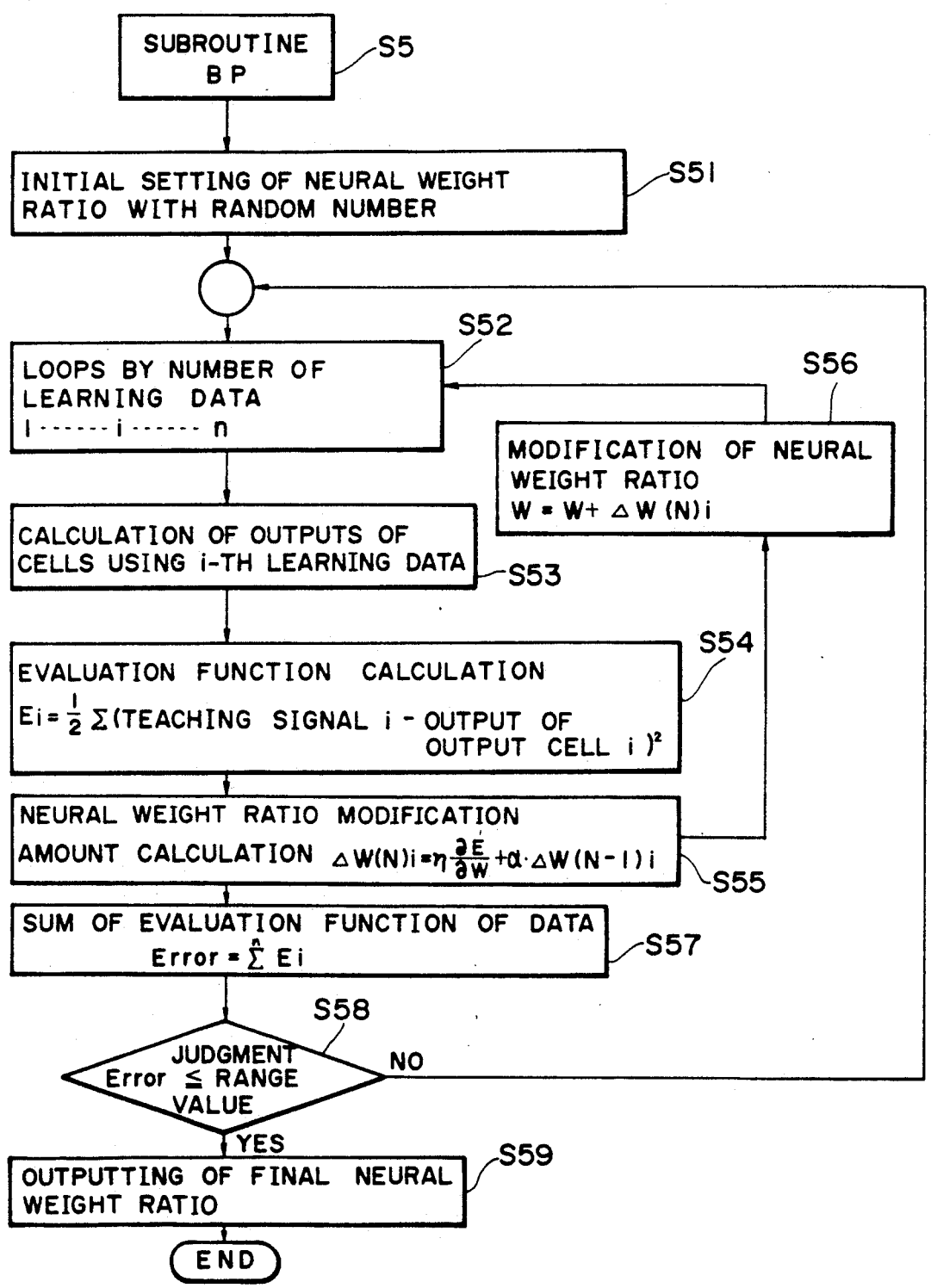
FIG. 5 is a view illustrating a back propagation method.

FIG. 5 illustrates an execution subroutine of back propagation (SUBROUTINE BP), and first at step S51, an initial value of a neural overlapping ratio is set with a random number. Then at step S52, a calculation is repeated by a number equal to the number of data for the learning. Then at step S53, an output of each cell is calculated. For such calculation of the output, the expression (2) given hereinabove is adopted in the present embodiment. Than at step S54, an evaluation function is calculated in accordance with the expression (3) given hereinabove. Subsequently, a neural overlapping ratio modification amount is calculated, at step S55, in accordance with the expression (8) given hereinabove in order to cause the evaluation function to have a minimum value. It is to be noted that the learning constant $\eta$ and the stability constant $\alpha$ are determined in accordance with experience, and for example, $\eta = 0.4$ and $\alpha = 0.6$. Then at step S56, the neural weight ratio is modified with the neural weight ratio modification amount, and then the control sequence returns to step S52 to execute the calculations repetitively. Accordingly, in the present embodiment, the neural weight ratio is modified for each leaning data. Further, in the present embodiment, a sum of the evaluation function of the individual data is calculated at step S57, and at step S58, it is judged whether the sum of the evaluation function is smaller than a determined range value. In particular, at step S58, it is judged whether or not the sum of errors is smaller than a predetermined value. Then, in case the value of the evaluation function is not yet smaller than the range value, the calculation is repeated again using the neural weight ratio at the point of time. Then, in case the sum of the evaluation function is smaller than the predetermined value, a final neural weight ratio is outputted at step S59. As a result, the SUBROUTINE BP comes to an end.

Subsequently, analogical inference of an abnormal visual field pattern using the multilayer neural network described above and learning in accordance with the back propagation method will be described in detail.

Figure 6:
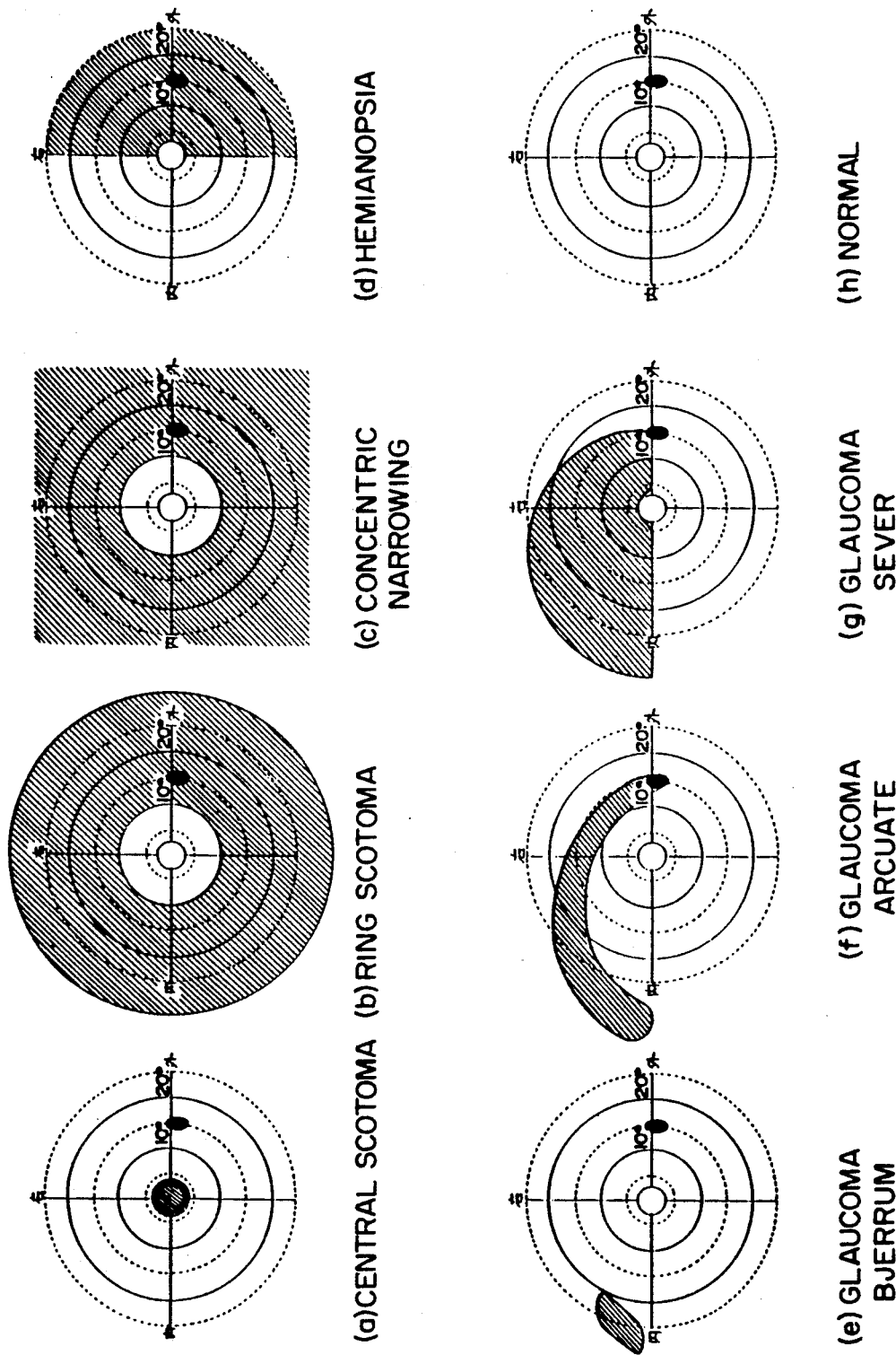
FIGS. 6 (a-h) are views showing typical examples of an abnormal visual field pattern.

First, typical patterns when the visual field is abnormal will be described with reference to FIG. 6. FIG. 6 shows dynamic quantitative visual fields of the right eye. It is to be noted that the right outer side is wider because the eye is the right eye.

(a) of FIG. 6 is a typical visual field pattern in the case of a central scotoma. This is the case wherein there is a scotoma at a central location of a visual field and can be seen in the case of a trouble of the retina at a yellow spot portion such as, for example, macular degeneration or central retinitis or a disease of a disc macular fiber bundle such as, for example, acute retrobulbar neuritis. (b) of FIG. 6 is a typical visual field pattern in the face of a ring scotoma. This is the case wherein the scotoma presents a ring profile surrounding a central portion and can be seen in the case wherein a Seidel-Bjerrum scotoma (a phenomenon wherein the Mariotte's spot is elongated and expanded upwardly and downwardly) proceeds in the case of glaucoma or even in the case of pigmentary degeneration of the retina. (c) of FIG. 6 is a typical visual field pattern in the case of concentric narrowing.

In the case of centripetal narrowing a visual field is narrowed to a substantially equal degree from the periphery toward the center in various directions. It can be seen, for example, at a last stage of glaucoma, pigmentary degeneration of the retina and so forth. It is to be noted that partial narrowing can be seen sometimes (settlement), and in the case of retinal detachment, narrowing can be seen at a portion corresponding to the detached portion. (d) of FIG. 6 is a typical visual field pattern in the case of hemianopsia. The hemianopsia is a condition wherein a visual field of a half side taking a vertical line passing a fixed visual point as a border is lost due to a trouble of a visual pathway. (e) of FIG. 6 is a typical visual field pattern in the case of glaucoma Bjerrum.

The glaucoma Bjerrum is a scotoma which can be seen in a region (Bjerrum region) around the center of the Mariotte's spot from upward and downward directions and is a characteristic of a glaucoma visual field. Such glaucoma Bjerrum is caused by a trouble of upwardly and downwardly extending neural fibers of the optic disc. (f) of FIG. 6 is glaucoma arcuate. Glaucoma Bjerrum normally appears in most cases in on or two upward and downward directions, and an extreme case of this is glaucoma arcuate. Glaucoma arcuate appears in the case of glaucoma. (g) of FIG. 6 is an glaucoma sever. The glaucoma sever is glaucoma arcuate which is elongated in either one of upward and downward directions so that it has such a shape that a doughnut is horizontally divided into two until it reaches a horizontal line of longitude on the opposite side to the yellow spot. A visual field at the stage is also called Renne step. Then, (h) of FIG. 6 is a visual field in the case of normality. It is to be noted that, while there is a vertically elongated scotoma, this is the Mariotte's spot. The reason why the Mariotte's spot. appears is that, because no optical cell is present at the optic disk, a visual field corresponding to the same makes a scotoma.

Accordingly, learning can be performed making use of such typical abnormal visual field patterns described above and a teaching signal. Here, such teaching signal is composed of a number of bits equal to the number of abnormal visual field patterns, and for example, where the number of abnormal patterns is 10. the teaching signal is composed of 10 bits and "0, 1, 0, 0, 0, 0, 0, 0, 0, 0".

Figure 7:
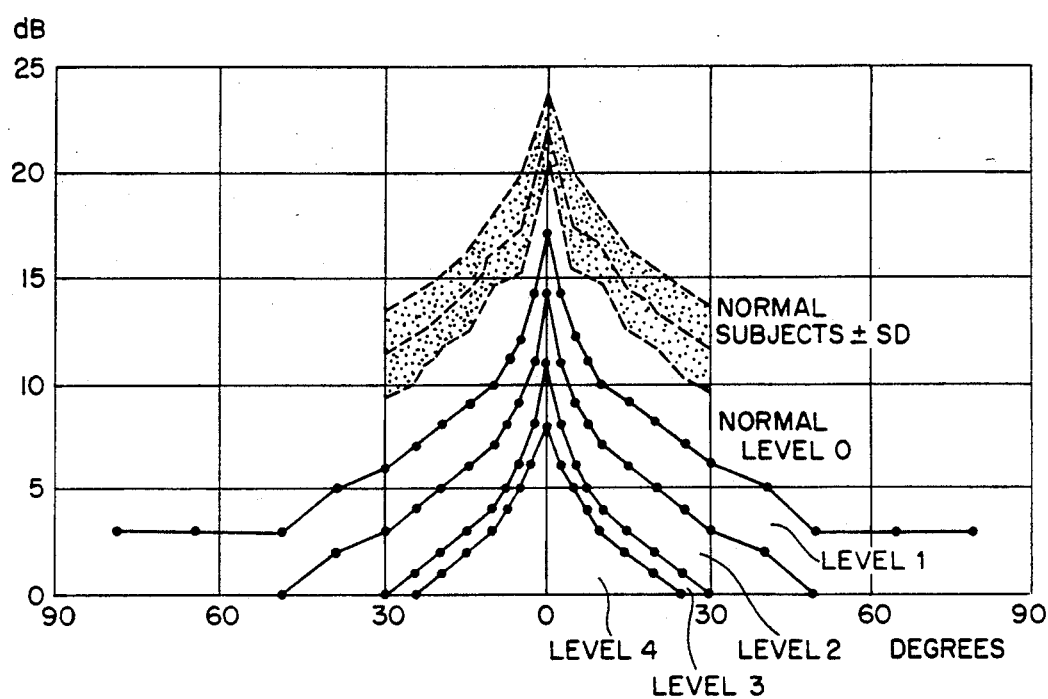
FIGS. 7 (a and b) are views illustrating a detailed result of measurement.
Figure 7:
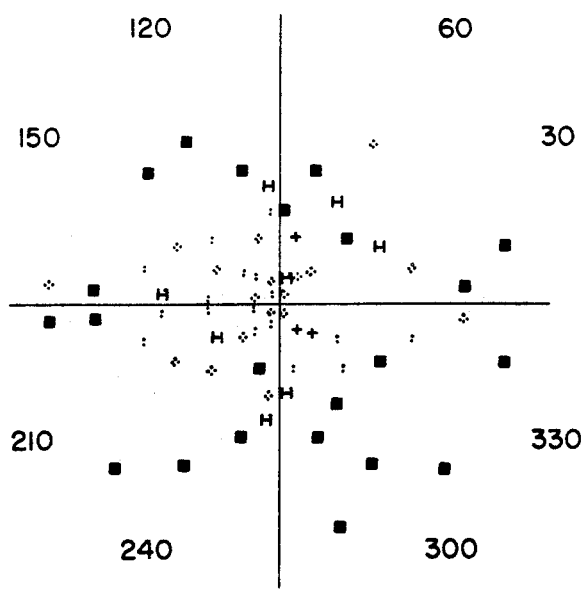

Subsequently, an example of a case wherein actual measurement is performed will be described with reference to FIG. 7. First, an average value and a standard deviation of measurement object persons having a normal visual field are shown in (a) of FIG. 7. Four levels are set based on this. A level higher by 5 decibels than the normal average is determined as LEVEL0 (normal), another level higher by 3 decibels than the LEVEL0 is determined as LEVEL1, a further level higher by further 3 decibels is determined as LEVEL2, a still further level higher by further 3 decibels is determined as LE- VEL3, and a maximum brightness is determined as LEVEL4. First, the target is presented at a brightness of the LEVEL0, and if this cannot be seen, then the brightness is raised successively to the LEVEL1 and to the LEVEL2. Then, a mark at a level at which the measurement object person can see the target is plotted, and such plotting is performed for each target. (b) of FIG. 7 shows an example wherein hemiamaurosis and narrowing of a visual field appear.

It is to be noted that, where not the typical abnormal patterns but results of actual measurement are utilized, the teaching signal may be, for example, "0.1, 0.0, 0.4, 0.5, 0.0, 0.0, 0.0, 0.0, 0.0, 0.0,".

Subsequently, operation of the perimetric instrument 1 of the present embodiment will be described with reference to the flow charts shown in FIGS. 8, 9 and 11 to 13.

FIRST EMBODIMENT

Measurement by way of a Measurer

Figure 8:
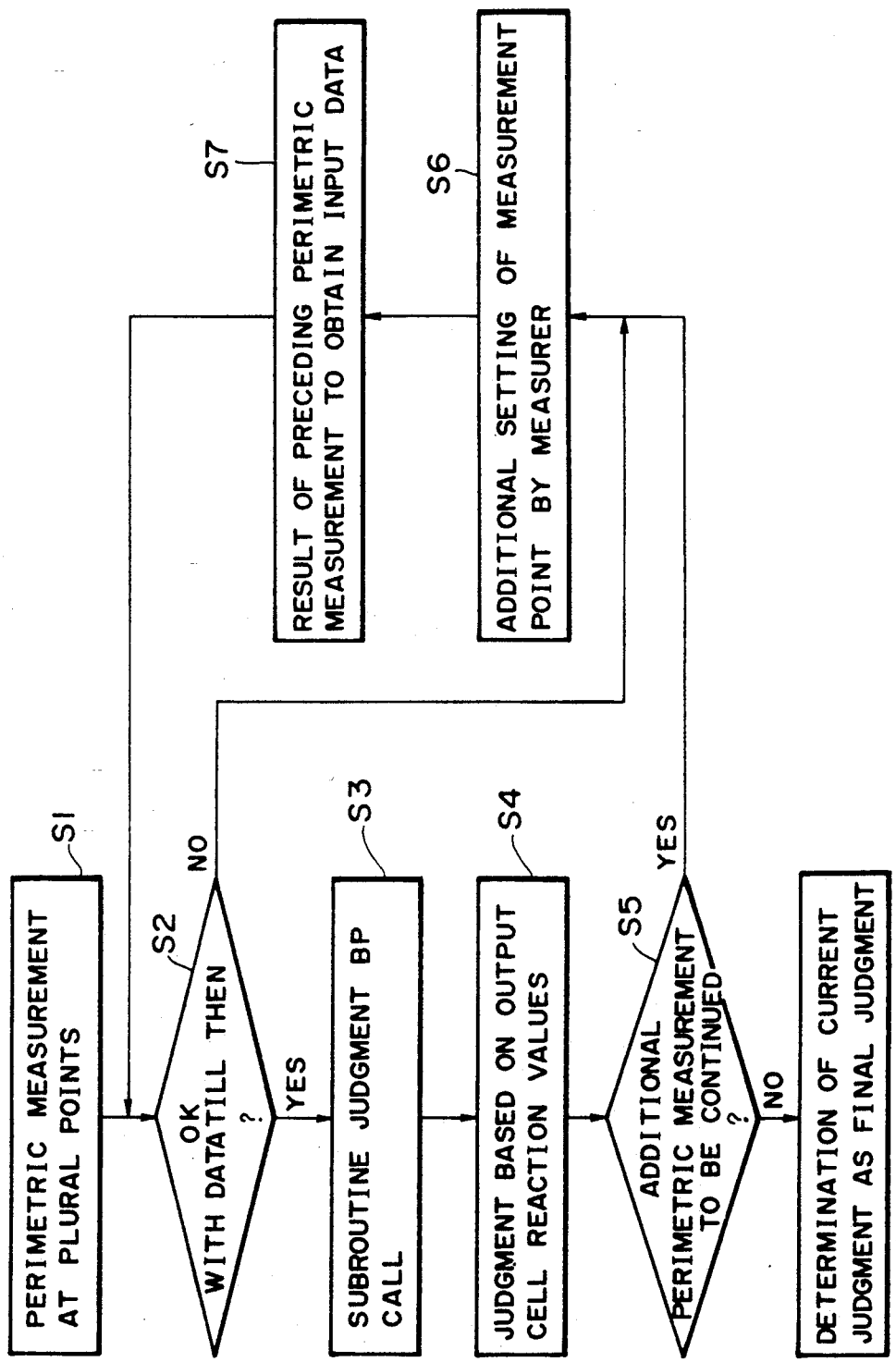
FIG. 8 is a view illustrating operation of a first embodiment.

First, measurement when a measurer acts as second will be described with reference to FIG. 8. If a measurer selects, at step S1, a necessary measurement program (for example, quick screening of a 71 point) by way of the operating section 7, then the CPU 9 reads in a corresponding program from the target projection program 5, and the program is executed. As a result, visual field measurement is performed at a plurality of points, and response data of the measurement object person are stored into the response storage section 6. Then at step S2, it is judged whether or not the response data are sufficient. In case the response data are sufficient, then the control sequence advances to step S3 at which the BP executing section 4 is started and the SUBROUTINE judgement BP is executed. It is to be noted that the SUBROUTINE judgement BP will be hereinafter described in detail. Then at step S4, judgement with respect to the abnormal visual field patterns is performed in accordance with the output cell response values calculated at step S3. Then at step S5, it is judged whether or not additional visual field measurement should be performed, and in case there is the necessity of continuing the measurement, the control sequence advances to step S6. On the other hand, in case additional visual field measurement is not necessary, the judgement at step S4 is maintained, and the abnormal visual field pattern which is the result of the judgement at step S4 is displayed on the display section 8.

It is to be noted that, at step S6, the measurer sets additional measurement points. The setting method is such that an additional measurement point is plotted on the TV monitor making use of, for example, the light pen or the like of the operating section 7 to set such additional measurement points. Thereupon, the operating section 7 functions as an addition instructing section. Then at step S7, data at the additional measurement points are added to the preceding data to make input data. It is to be noted that, in case the data are novel, the data are used as they are.

Meanwhile, in case the response data are not sufficient at step S2, the control sequence advances to step S6 at which additional measurement points are set.

Figure 9:
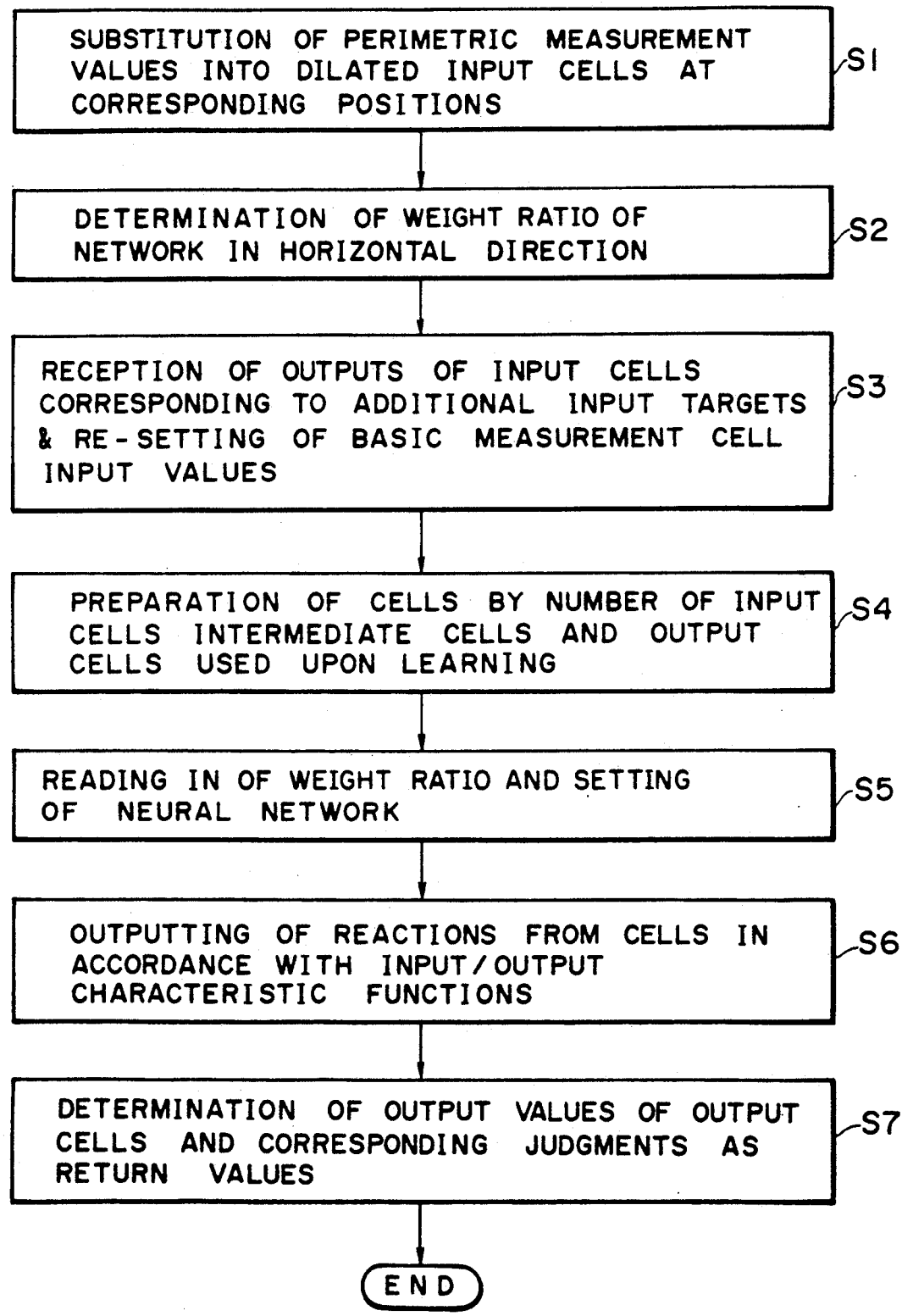
FIG. 9 is a view illustrating a subroutine of judgment BP.

Here, the SUBROUTINE judgment BP will be described in detail with reference to FIG. 9. First at step S1, visual field measurement values are substituted into dilated input cells corresponding to the positions thereof. The dilated input cells have a construction of a radial network locally (a small area around a measurement point of basic measurement) in the input layer different from a construction of back propagation of the conventional type. Accordingly, cells other than those cells which correspond to basic measurement will be hereinafter referred to as dilated input cells.

Subsequently at step S2, a weight ratio of the network in a horizontal direction is determined. Further at step S3, outputs of input cells corresponding to an additional input index are received, and basic measurement cell input values are set again. Then at step S4, a number of cells equal to the number of input cells, intermediate cells and output cells which have been used upon learning are prepared. Then at step S5, a neural weight ratio interconnecting cells which has been calculated in advance by the learning back propagation system is read in from a file, and the neural network is set. Further at step S6, the individual cells of the neural network constituted at step S5 output their reactions in accordance with input/output characteristic functions. Then at step S7, the output values of the individual cells at step S6 and the name of a corresponding abnormal visual field pattern (judgment) are determined as return values, and then the control sequence comes to an end.

Subsequently, treatment of responses of additional measurement points will be described in detail with reference to FIG. 10. It is necessary to devise responses of additional measurement points so that they may be provided to responses of the basic measurement target (measurement index before addition) in the proximity of additional measurement points. Thus, such an additional measurement target NO. 1 as shown in (a) of FIG. 10 can be set. The additional measurement target NO. 1 is set such that the basic measurement targets NO. 10, NO. 11 and NO. 12 may exist within a circle of the radius $r_m$ centered at the additional measurement target NO. 1. Then, if the distances from the additional measurement target NO. 1 to the basic measurement targets NO. 10, NO. 11 and NO. 12 are represented by $r_1$, $r_2$ and $r_3$, then $r_1 \leq r_2$ and $r_2 \leq r_3$.

Then, a response to the additional measurement target and responses to the basic measurement targets are coupled to each other by a radial network. Then, while the weight ratio of the network is determined in response to a distance, a method of determining an weight ratio which increases in inverse proportion to a distance will be described as an example. In other words, an weight ratio is determined in inverse proportion to a distance using a shortest distance as a minimum unit.

For example, describing the case wherein the response to the basic measurement target NO. 10 is 2, the response to the basic measurement target NO. 11 is 2, the response to the basic measurement target NO. 12 is 3 and then the response to the additional measurement target NO. 1 is 4, input data at NO. 10 can be determined as $$\frac{1}{2}\left(2 + \frac{r_1}{r_1} \times 4\right)$$

input data at NO. 11 as $$\frac{1}{2}\left(2 + \frac{r_1}{r_2} \times 4\right)$$

and input data at NO. 12 as $$\frac{1}{2}\left(2 + \frac{r_1}{r_3} \times 4\right)$$

In particular, if input data are represented in a general expression, then $$\text{Input data} = \frac{1}{(1 + \text{additional index number})} \left\{ \text{basic response} + \frac{r_1}{r_2} \begin{pmatrix} \text{response to} \\ \text{addition} \\ \text{NO. 1} \end{pmatrix} + \frac{r_1}{r_2} \begin{pmatrix} \text{response to} \\ \text{addition} \\ \text{NO. 2} \end{pmatrix} \ldots \right\} \quad (9)$$

$$= \frac{1}{(n+1)} \left\{ \text{basic response} + \sum_{k=1}^{n} \frac{r_1}{r_k} \times A(k) \right\}$$

where $r_1 \leqq r_2$ $r_1 \leqq r_3$

... response to additional measurement

... target NO. ($k$) is represented as $A(k)$.

...

Figure 10A:
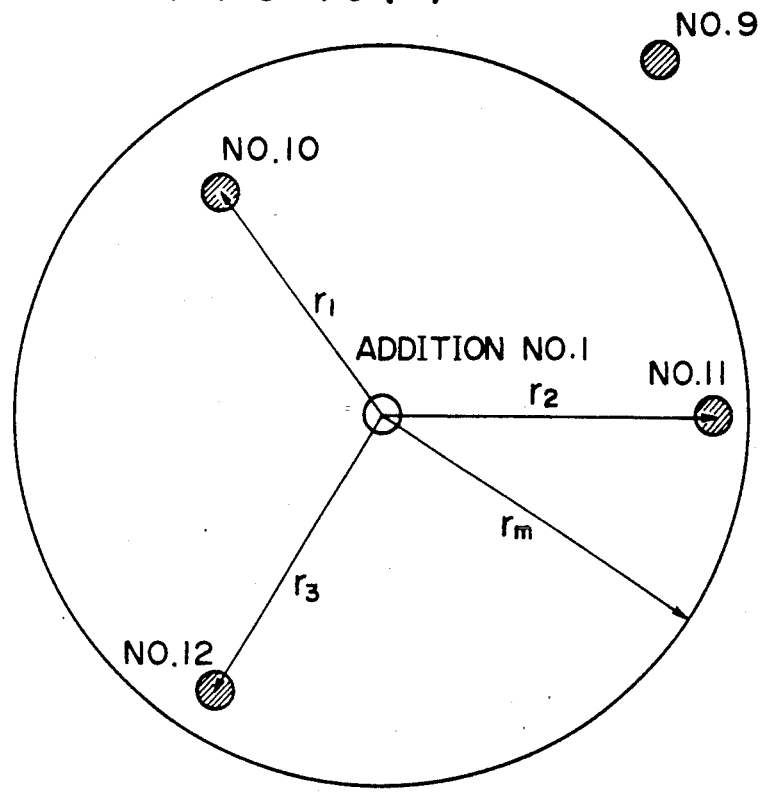
FIGS. 10(a & b) are views illustrating an additional measurement target.
Figure 10B:
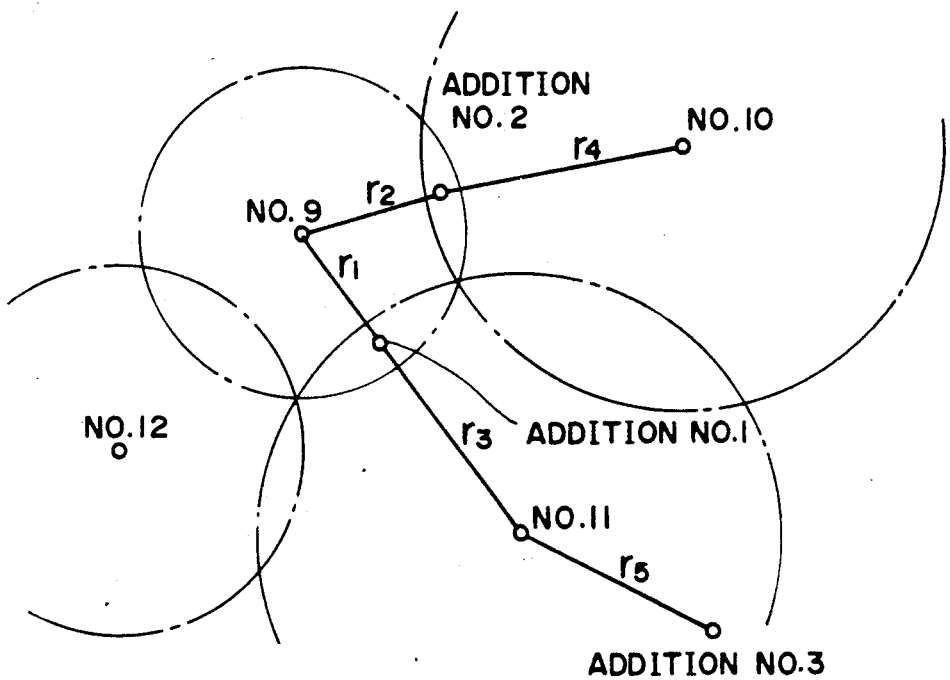

$r_1 \leqq r_n$  $n$: additional measurement target number $r_1$: minimum distance among $r_1$ to $r_n$ It is to be noted that areas around a basic measurement index are provided in a somewhat overlapping relationship as shown in (b) of FIG. 10. A response to an additional measurement target is devised so that it may have an influence on a response to a basic measurement target of an area in which it is included. In particular, where a plurality of additional measurement targets are present in an area of a certain basic measurement target, the response to the basic measurement target is corrected in accordance with a value inversely proportional to the distance thereof using a minimum one of the distances of the additional measurement targets as a unit distance. Then, a basic general expression is similar to the expression (9) given hereinabove.

Further, such area is not limited to a circular shape and may be a rectangular shape or the like. Further, while the size of the area can be determined suitably, since it is necessary to examine a portion around the center with accuracy, it is desirable to make the area small.

SECOND EMBODIMENT

Subsequently, operation of the perimetric instrument 1 of the present embodiment will be described with reference to the flow charts shown in FIGS. 11 and 12.

Figure 11:
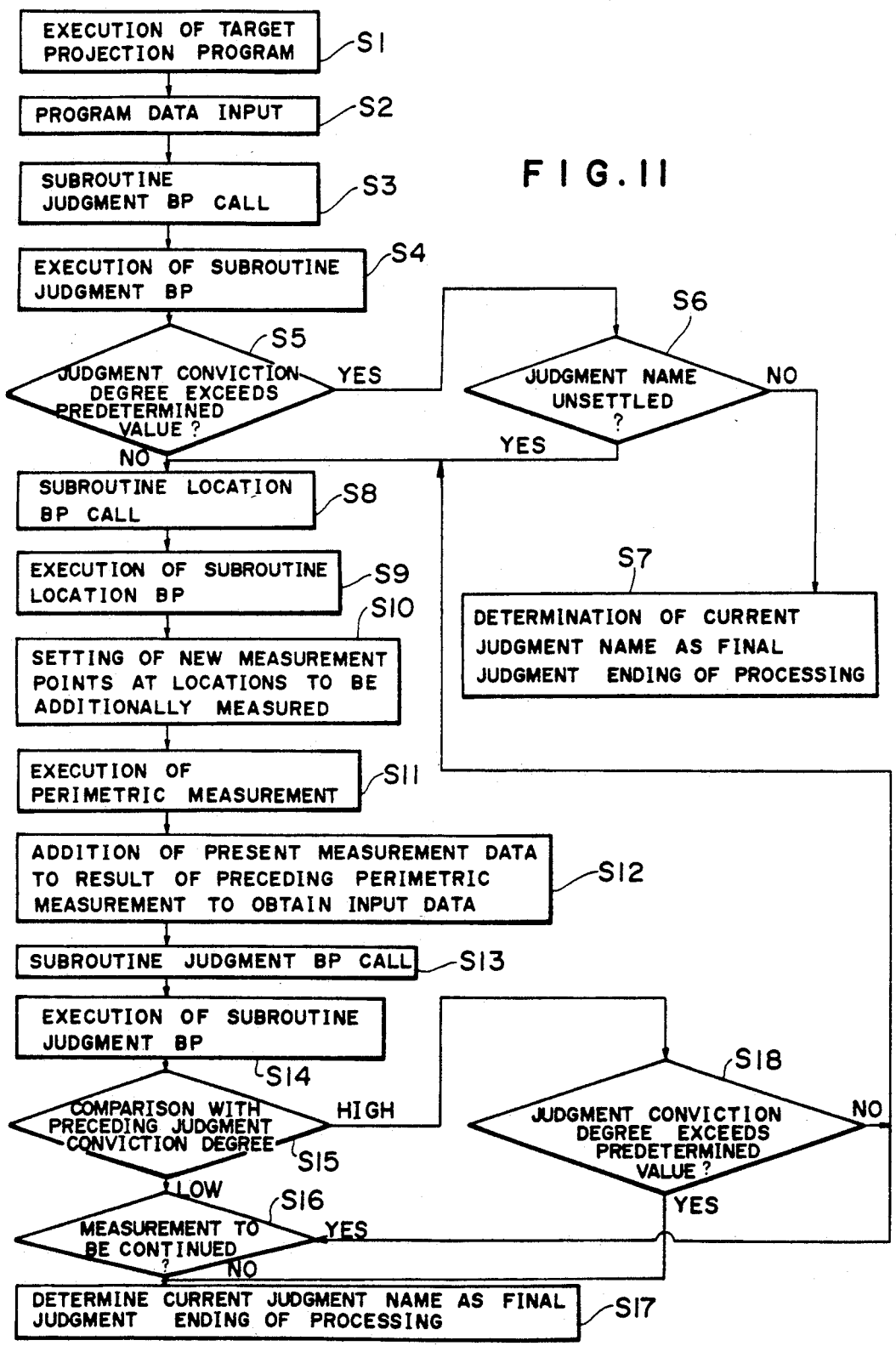
FIG. 11 is a view illustrating operation of a second embodiment.
Figure 12:
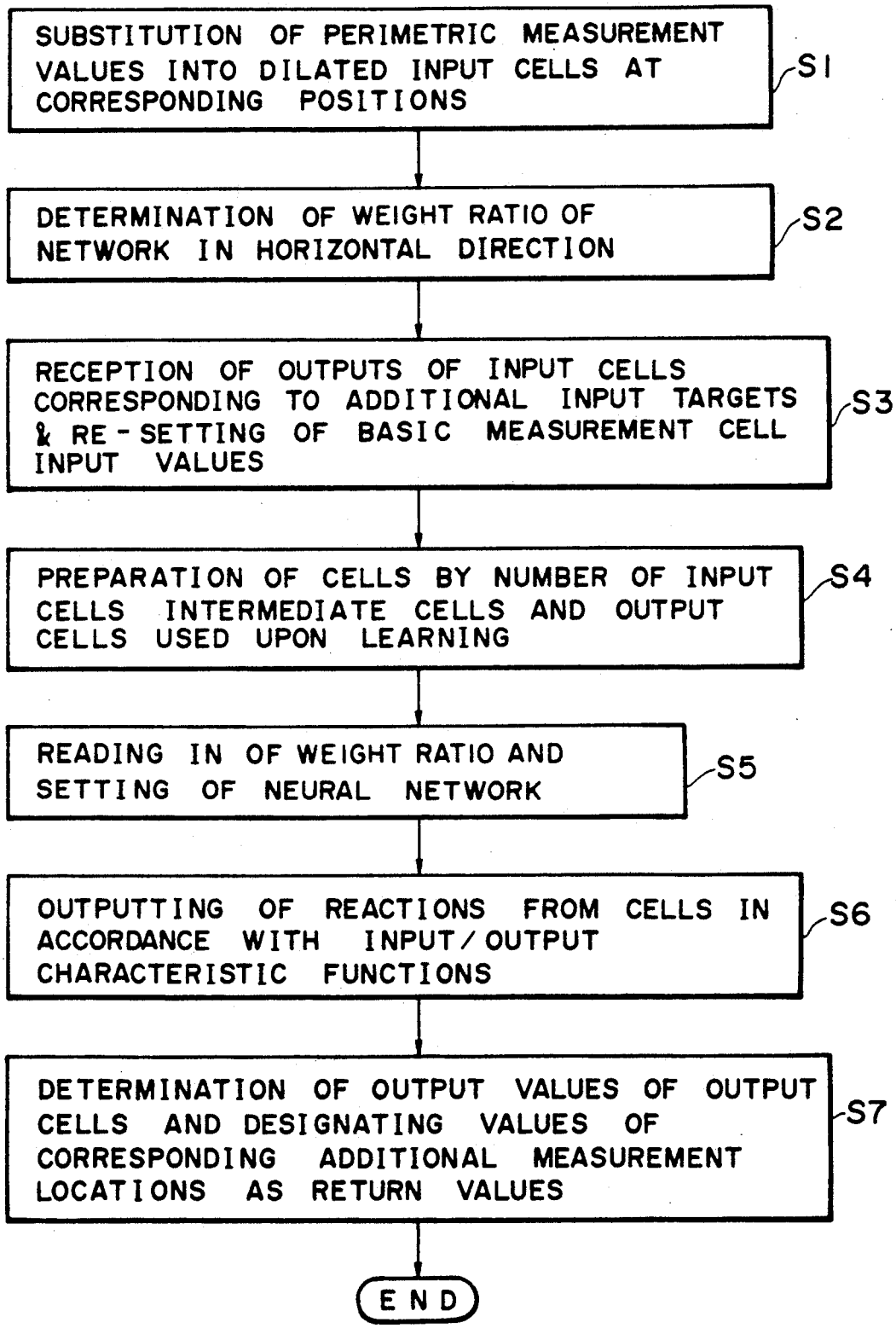
FIG. 12 is a view illustrating a subroutine of location BP.

FIG. 11 illustrates operation of the second embodiment wherein all basic measurement targets are first presented and then an abnormal visual field pattern is analogically inferred, whereafter an additional measurement target is determined. First at step S1, a program instructed by a measurer is recalled from the target projection program storage section 5 and executed. For example, a program of quick screening of a 71 point can be executed. Then at step S2, data of the program read in at step S1 are inputted as input values. Subsequently, the SUBROUTINE judment BP is called at step S3 and then executed at step S4. It is to be noted that the SUBROUTINE judgment BP has been described in detail hereinabove with reference to FIG. 9. As a result of execution at step S4, judgment of an abnormal visual field pattern is performed. Then at step S5, it is judged whether the judgment conviction degree of the judgment at step S4 exceeds a predetermined value. In the present embodiment, the predetermined value is set to 50%, and in case the judgment conviction degree is higher than 50%, the control sequence advances to step S6. At step S6, it is determined whether an abnormality judgment name of the visual field has been determined.

In case the judgment name is allowable, the control sequence advances to step S7 at which the abnormality judgment name of the visual field is determined decisively, and the control sequence comes to an end. On the other hand, in case an abnormality judgment name of the visual field has not been determined at step S6, the control sequence advances to step S8. At step S8, a SUBROUTINE location BP is read in. Then at step S9, the SUBROUTINE location BP is executed. As a result of execution of the SUBROUTINE location BP, additional measurement locations to be added after then are forecast. It is to be noted that the SUBROUTINE location BP will be hereinafter described in detail with reference to FIG. 12. In particular, locations to be additionally measured are forecast in accordance with the abnormal visual field pattern judged at step S4. For example, in case the abnormal visual field pattern judged at step S4 seems a central scotoma shown in (a) of FIG. 6, additional measurement locations to be added are disposed in a high density in the neighborhood of a border area of the central scotoma. On the other hand, in case the abnormal visual field pattern judged at step S4 seems ring scotoma shown in (b) of FIG. 6, additional measurement locations to be added are disposed in a high density in the neighborhood of a border area of the ring scotoma. Similarly, in case it is judged that the abnormal visual field pattern judged at step S4 seems narrowing of a visual field shown in (c) of FIG. 6, additional measurement locations to be added are disposed in a high density in the neighborhood of a border area of a peripheral scotoma. In case it is judged that the abnormal visual field pattern seems a Bjerrum scotoma (which seems to arise from glaucoma) shown in (e) of FIG. 6, additional measurement locations to be added are disposed in a high density in the proximity of the Mariotte's spot and in the neighborhood of the Bjerrum area (annular area near 10 degrees). Then, in case it is judged that the abnormal visual field pattern seems arcuate scotoma (which seems to arise from glaucoma) of (f) of FIG. 6, additional measurement locations to be added are disposed in a high density around the Bjerrum area. Further, in case it is judged that the abnormal visual field pattern seems a glaucoma sever (which seems to arise from glaucoma) of (g) of FIG. 6, additional measurement locations to be added are disposed in a high density at a further periphery than that of glaucoma arcuate Then, in case it is judged that the visual field pattern is a normal visual field shown in (h) of FIG. 6, additional measurement locations to be added are presented in accordance with the basic program.

Subsequently at step S10, measurement points are set at random in the additional measurement locations. Then at step S11, measurement is performed. Subsequently at step S12, data measured at step S11 are added to a result of the preceding visual field measurement to obtain input data. Further at step S13, the SUBROUTINE judgment BP is executed again to effect judgment of abnormality of the visual field. Then at step S15, the judgment at step S14 and the judgment conviction degree of the judgment at step S4 are compared with each other, and in case the judgment conviction degree at step S14 is lower, the control sequence advances to step S16. At step S16, judgment of the measurer is requested whether or not the measurement is to be continued, and in case measurement should not be continued, the control sequence advances to step S17 at which the current judgement name is determined as a judgment name of the abnormal visual field, thereby completing the measurement. Then, the judgment name and so forth are displayed on the display section 8. On the other hand, in case the measurement should be continued, the control sequence returns to step S8 to execute the SUBROUTINE location BP.

It is to be noted that, in case the judgment conviction degree at step S14 is higher at step S15, the control sequence advances to step S18 at which it is judged whether the judgment conviction degree exceeds a predetermined value, and in case it exceeds the predetermined value, the control sequence advances to step S17 and the measurement is completed. On the other hand, in case the diagnosis conviction degree does not exceed the predetermined value at step S18, the control sequence returns to step S8 to execute the SUBROUTINE location BP again.

Subsequently, the SUBROUTINE location BP will be described with reference to FIG. 12. The subroutine forecasts additional measurement locations to be added making use of a learning method based on back propagation. Accordingly, it has a similar construction to the judgment of an abnormal visual field pattern illustrated in FIG. 9. In particular, the steps S1 to S6 are similar to those of the SUBROUTINE judgment BP of FIG. 9. Then at step S7, output values of the individual cells at step S6 and designating values of corresponding additional measurement locations to be measured after then are determined as return values, and then the control sequence comes to an end.

THIRD EMBODIMENT

Subsequently, a third embodiment of the perimetric instrument 1 will be described with reference to FIG. 13. The third embodiment analogically infers an abnormal visual field pattern while presenting a basic measurement target and determines another basic measurement target to be presented.

First at step S1, a measurement program designated by a measurer is read in from the target projection program storage section 5, and measurement is performed for several measurement points. For example, measurement for the first 5 points of quick screening of a 71 point is performed. Subsequently at step S2, data of the present measurement are added to a result of preceding visual field measurement to obtain input data. It is to be noted that, in case the measurement is new measurement, the data are used as they are. Then at step S3, the SUBROUTINE judgment BP is called, and then at step S4, the SUBROUTINE judgment BP is executed to judge an abnormal visual field pattern based on output cell value response values. Further at step S5, a judgment conviction degree is compared with a preceding judgment conviction degree, and in case it is lower than the preceding judgment conviction degree, the control sequence advances to step S6 at which it is requested for a measurer to make judgment whether the measurement should be continued. In case the measurer does not want to continue the measurement at step S6, a current judgment name is determined as a final judgment at step S7, and the control sequence comes to an end.

In case the diagnosis conviction degree is higher than the preceding diagnosis conviction degree at step S5, the control sequence advances to step S8. At step S8, it is judged whether or not the judgment conviction degree exceeds a predetermined value, and in case it exceeds the predetermined value, the control sequence advances to step S7 and the measurement is completed. In case the judgment conviction degree does not exceed the predetermined value at step S8, the control sequence advances to step S9. At step S9, the SUBROUTINE location BP is called, and then at step S10, the SUBROUTINE location BP is executed to forecast additional measurement locations to be measured and set new measurement points. Then, the control sequence returns to step S2 to continue the measurement.

It is to be noted that the third embodiment is simple in construction comparing with the second embodiment and has an effect that a measurement time can be reduced because automatic measurement is performed from the beginning.

Figure 14A:
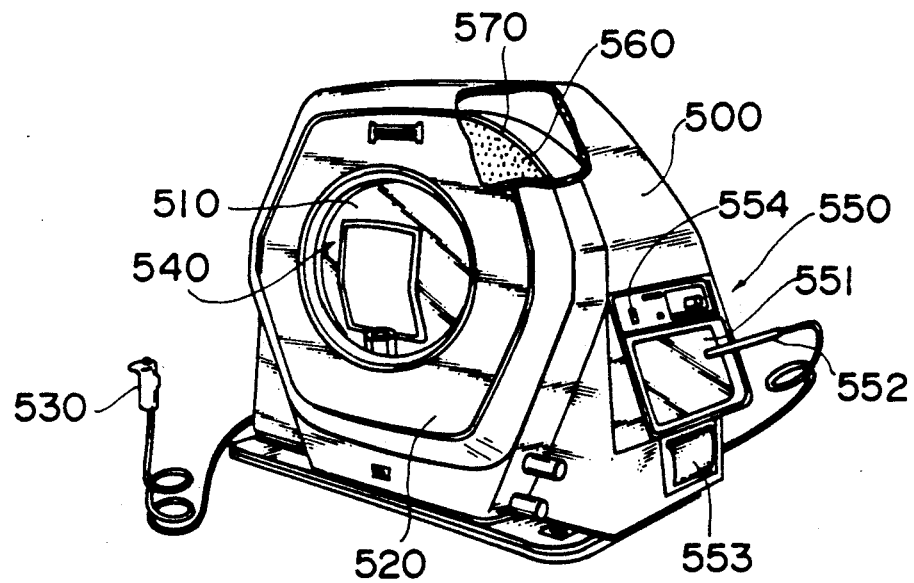
FIGS. 14(a & b) are views illustrating a modification which employs LEDs for a screen.

Subsequently, a modification to the present embodiment will be described. First, a perimetric instrument 1 of the fixed target type will be described with reference to FIG. 14. While the perimetric instrument of the embodiment described above is constituted such that the rotary mirror 400 is rotated to move the target presentation location I, it is possible to bury a light source such as an LED as a target on a screen. (a) of FIG. 14 shows an appearance of a perimetric instrument 1 of the LED type, and the perimetric instrument 1 is constituted from a housing 500, a panel 520 mounted on the front side of the housing 500 and having a circular hole 510 formed therein for receiving the face of a measurement object person, a recognition switch 530, a measurement object eye fixing section 540 for fixing an object eye of a measurement object person to a predetermined position, an operation display device 550 formed on a side wall of the housing 500, and a hemispherical dome formed in the housing 500 and having a plurality of LEDs 560 mounted thereon.

The operation display device 550 has a TV monitor 551, a light pen 552, a printer 553, a control switch 554 and so forth mounted thereon.

Subsequently, a construction of an electric system will be described with reference to (b) of FIG. 14. Inputted to an I/O interface 600 are output signals of the light pen 552 and control switch 554 which are operated by a measurer, a recognition signal from the recognition switch 530 for inputting whether or not a measurement object person has recognized a target, and an initial measurement program selecting signal from an initial measurement program selecting section 610. The I/O interface 600 converts the input signals into different signals suitable for the processing in an internal device and converts a result of measurement into a signal with which it can be printed easily. Further, a response storage section 645 is provided for storing a response therein in response to a recognition signal from the recognition switch 530.

A CPU 620 executes principal control and so forth of the perimetric instrument 1 of the present modification.

An LED matrix interface 630 is an interface for lighting the LEDs 560 in accordance with target presentation conditions read in by the CPU 620 and includes at least two transistor arrays which make a matrix.

A presentation condition storage section 640 stores therein programs for realizing target presentation conditions (a combination of a lighting intensity, a position, a lighting time and so forth) which specify how the LEDs 560 of the hemispherical dome 570 are to be lit. For example, a screening measurement program and so forth are stored in the presentation condition storage section 640.

A GDC (graphics display controller) receives an LED arrangement signal, a selected measurement program, a signal indicative of a position of an LED in a lit condition and a response signal described hereinabove and forms an image signal for causing the TV monitor 551 to display such information and then outputs the image signal to a video memory 660. A timing controlling circuit 670 forms a suitable timing signal from a clock signal outputted from a clock oscillator 680 and outputs the timing signal to the GDC 650, CPU 620 and video memory 660.

A P/S converter 690 converts a parallel digital signal from the video memory 660 into a serial signal to form a video signal and outputs the video signal to the TV monitor 551.

It is possible to add, to the perimetric instrument 1 of the LED type having such construction as described above, an abnormal visual field pattern analogical inferring function which employs the multilayer neural network of the present embodiment.

Figure 15:
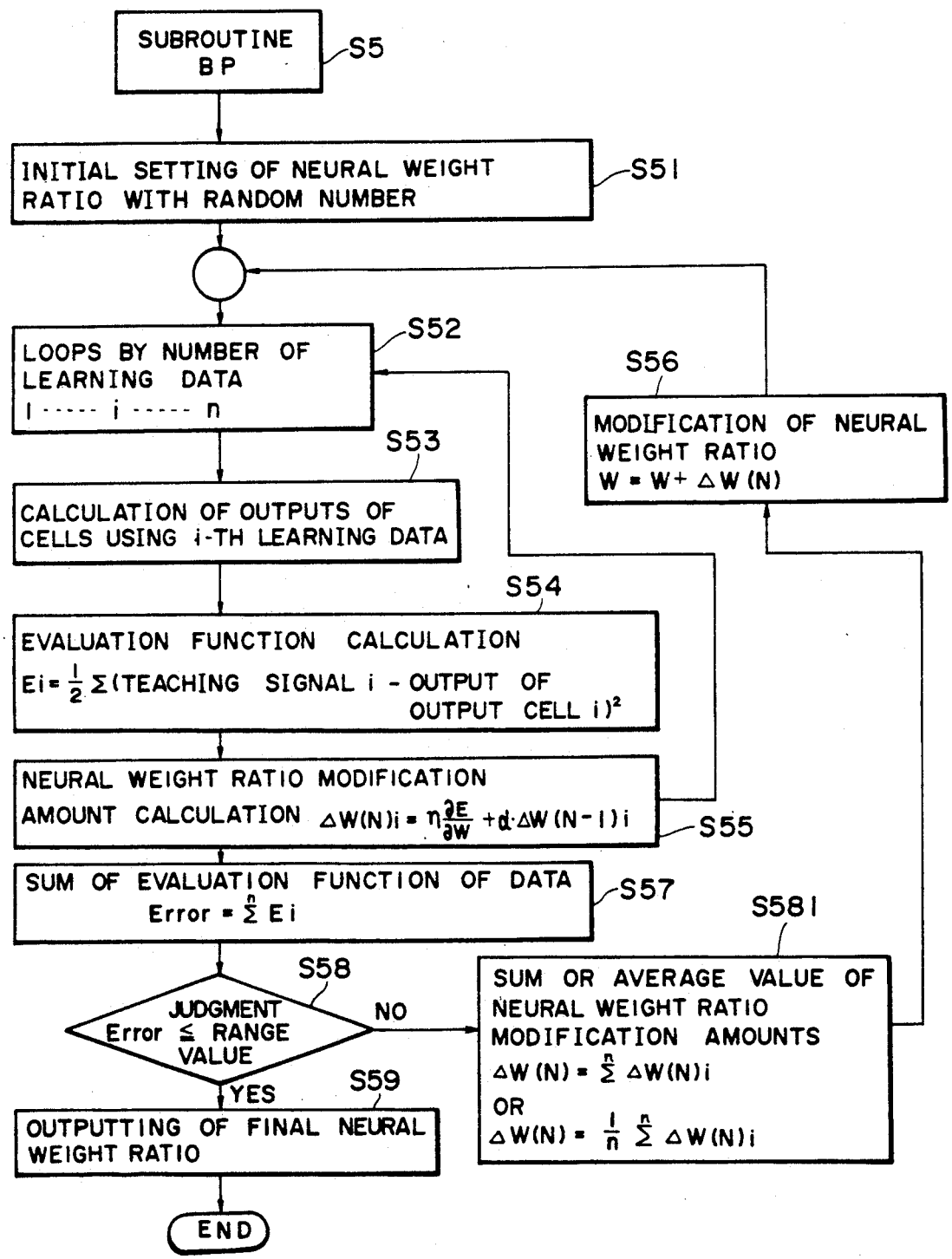
FIG. 15 is a view illustrating a modification of the back propagation method.

Subsequently, a modification regarding learning of the multilayer neural network will be described with reference to FIG. 15.

According to the subroutine of back propagation described above, an evaluation function is calculated for each learning data, and a neural weight ratio is modified in accordance with the evaluation function and then a calculation is performed repetitively. On the other hand, in the present embodiment, a neural weight ratio modification amount is calculated and stored at step S55. Further at step S57, a sum of the evaluation function of individual data is calculated, and it is judged at step S58 whether or not the sum (Error) is smaller than a determined range value. Then, in case the sum (Error) is greater than the range value, a sum of individual neural weight ratio modification amounts or an average value of individual neural weight ratio modification amounts is calculated at step S581. Then at step S56, the individual neural weight ratios are modified with the modification amounts calculated at step S581, and a repetitive calculation is continued using the neural weight ratios. Accordingly, in the present embodiment, neural weight ratio correction amounts for all learning data are first calculated and then modified collectively. Then, in case it is judged at step S58 that the sum of the evaluation function has become smaller than the range value, then the control sequence advances to step S59. Since the other steps are similar to those of the subroutine of FIG. 5, description thereof will be omitted herein.

It is to be noted that, while the present embodiment is described with the example wherein it is applied to a static perimetric instrument, it can naturally be applied also to a dynamic perimetric instrument.

According to the present invention having such construction as described above, the index presenting section presents a measurement target, and the responding section gives a response of presence or absence of recognition of the measurement target by a measurement object person. The multilayer neural network which includes an input layer, hidden layers and an output layer introduces a neural weight ratio determined in accordance with responses when the visual field is normal and when the visual field is abnormal, and as a response from the responding section is inputted to the input layer while an output from the output layer is sent out to the analogical inferring section, the analogical inferring section can analogically infer an abnormal visual field pattern of the measurement object person. Accordingly, there are such excellent effects that an abnormal visual field pattern of the measurement object person can be analogically inferred and that it is possible to help judgment of an abnormal visual field pattern by a measurer. Since also labor, time and so forth of a measurer are reduced, burdens to the measurer and a measurement object person can be reduced remarkably.

Further, according to the present invention, the additional target section presents additional measurement targets other than basic measurement targets on the target presenting section, and in case there is a response to the additional targets, the input data section determines input data to the input layer of the multilayer neural network described above in connection with responses to the basic measurement targets in the neighborhood of the additional measurement targets. Accordingly, there is an effect that, even in case data are insufficient, a measurer can add measurement targets which are considered necessary. Accordingly, there is an excellent effect that a measurer can effect suitable judgment of an abnormal visual field pattern.

Further, according to the present invention, since the addition instructing section can determine additional measurement targets in accordance with an abnormal visual field pattern analogically inferred by the analogical inferring section and present the additional measurement targets to the target presenting section, judgment can be performed with a high degree of reliability, and since the measurement time is reduced, there is an excellent effect that a pain to a measurement object person is reduced. Further, since the input data determining section can also determine, when there is a response to an additional measurement target, input data to the input layer of the multilayer neural network described above in connection with responses to basic measurement targets in the neighborhood of the additional measurement target, data of the additional measurement targets can be made use of appropriately, and there is an effect that measurement can be performed with a high degree of accuracy.

Further, according to the present invention, while the analogical inferring section presents basic measurement targets, responses till then are inputted as input data to the input layer of the multilayer neural network described above and an abnormal visual field pattern of the measurement object person is analogically inferred from an output of the output layer then. Then, the addition instructing section can determine basic measurement targets to be presented after then in accordance with an abnormal visual field pattern analogically inferred by the analogical inferring section and present the basic measurement targets to the target presenting section. Accordingly, there is an excellent effect that the measurement time can be reduced comparing with a perimetric instrument which presents all basic measurement targets and add additional measurement targets to those basic measurement targets.

I claim:

1. A perimetric instrument, characterized in that it has a target presenting section for presenting a measurement target, a responding section for giving a response whether or not a measurement object person has recognized the presented target, a multilayer neural network having an input layer, hidden layers and an output layer and having a neural weight ratio which is determined in advance based on a normal response and typical responses when the visual field of a measurement object person is abnormal, and an analogical inferring section for inputting a response from said responding section to said input layer of said multilayer neural network and analogically inferring an abnormal visual field pattern of a measurement object person from an output of said output layer then.

2. A perimetric instrument, characterized in that it has a target presenting section for presenting one of predetermined basic measurement targets, a responding section for giving a response whether or not a measurement object person has recognized the presented target, a multilayer neural network having an input layer which consists of a number of input cells equal to the number of the basic measurement targets, hidden layers and an output layer which consists of a divisional number of output cells and having a neural weight ration which is determined in advance based on a normal response and typical responses when the visual field of a measurement object person is abnormal, an analogical inferring section for inputting a response from said responding section as input data to said input layer of said multilayer neural network and analogically inferring an abnormal visual field pattern of a measurement object person from an output of said output layer then, an addition instructing section for causing said target presenting section to present additional measurement targets other than the basic measurement targets, and an input data determining section for determining, when there is a response to one of the additional measurement targets, input data to said input layer of said multilayer neural network in connection with responses to those basic measurement targets around the additional measurement target.

3. A perimetric instrument, characterized in that it has a target presenting section for presenting one of predetermined basic measurement targets, a responding section for giving a response whether or not a measurement object person has recognized the presented target, a multilayer neural network having an input layer which consists of a number of input cells equal to the number of the basic measurement targets, hidden layers and an output layer which consists of a number of output cells equal to the number of abnormal visual field patterns and having a neural weight ratio which is determined in advance based on a normal response and typical responses when the visual field of a measurement object person is abnormal, an analogical inferring section for presenting the basic measurement targets, inputting, when a response is obtained, the response as input data to said input layer of said multilayer neural network and analogically inferring an abnormal visual field pattern of a measurement object person from an output of said output layer then, and an addition instructing section for determining additional measurement targets in accordance with the abnormal visual field pattern analogically inferred by said analogical inferring section and causing said target presenting section to present the additional measurement targets.

4. A perimetric instrument according to claim 3, further comprising an input data determining section for determining, when there is a response to one of the additional measurement targets, input data to said input layer of said multilayer neural network in connection with responses to those basic measurement targets around the additional measurement target.

5. A perimetric instrument, characterized in that it has a target presenting section for presenting one of predetermined basic measurement targets, a responding section for giving a response whether or not a measurement object person has recognized the presented target, a multilayer neural network having an input layer which consists of a number of input cells equal to the number of the basic measurement targets, hidden layers and an output layer which consists of a number of output cells equal to the number of abnormal visual field patterns and having a neural weight ratio which is determined in advance based on a normal response and typical responses when the visual field of a measurement object person is abnormal, an analogical inferring section for inputting, while the basic measurement targets are presented, responses till then as input data to said input layer of said multilayer neural network and analogically inferring an abnormal visual field pattern of a measurement object person from an output of said output layer then, and an addition instructing section for determining, in accordance with the abnormal visual field pattern analogically inferred by said analogical inferring section, those basic measurement targets to be presented after then and causing said target presenting section to present the basic measurement targets.

* * * * *

UNITED STATES PATENT AND TRADEMARK OFFICE
CERTIFICATE OF CORRECTION

PATENT NO. : 5,108,170
DATED : April 28, 1992
INVENTOR(S) : Akihiro Sugiyama

It is certified that error appears in the above-identified patent and that said Letters Patent is hereby corrected as shown below:

Column 2, line 21, "measure a" should read --measure at--;

Column 8, line 1, "face" should read --case--;

Column 8, line 34, "on or" should read --one of--;

Column 15, line 53, "repetitiely" should read --repetitively--;

Column 17, line 41, "ration" should read --ratio--.

Signed and Sealed this

Seventh Day of December, 1993

BRUCE LEHMAN

Attest:

Attesting Officer

Commissioner of Patents and Trademarks